United States Patent
Kingsley (10) Patent No.: US 8,323,310 B2
(45) Date of Patent: Dec. 4, 2012

(54) VESSEL SEALING JAW WITH OFFSET SEALING SURFACE

(75) Inventor: Dylan R. Kingsley, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 557 days.

(21) Appl. No.: 12/569,710

(22) Filed: Sep. 29, 2009

(65) Prior Publication Data

US 2011/0077649 A1    Mar. 31, 2011

(51) Int. Cl.
A61B 17/29    (2006.01)
A61B 18/14    (2006.01)

(52) U.S. Cl. ............... 606/207; 606/51; 606/52
(58) Field of Classification Search ........ 606/51, 606/52, 205–207
See application file for complete search history.

(56) References Cited

U.S. PATENT DOCUMENTS

| | | | |
|---|---|---|---|
| 5,171,257 A * | 12/1992 | Ferzli | 606/205 |
| 5,261,917 A * | 11/1993 | Hasson et al. | 606/139 |
| 5,389,104 A | 2/1995 | Hahnen et al. | |
| 5,507,773 A * | 4/1996 | Huitema et al. | 606/207 |
| 5,688,270 A * | 11/1997 | Yates et al. | 606/51 |
| 5,725,536 A | 3/1998 | Oberlin et al. | |
| 5,810,805 A | 9/1998 | Sutcu et al. | |
| 6,017,358 A | 1/2000 | Yoon et al. | |
| H2037 H | 7/2002 | Yates et al. | |
| 6,669,696 B2 | 12/2003 | Bacher et al. | |
| 7,083,620 B2 * | 8/2006 | Jahns et al. | 606/51 |
| 8,016,827 B2 | 9/2011 | Chojin | |
| 8,142,473 B2 | 3/2012 | Cunningham | |
| 8,162,973 B2 | 4/2012 | Cunningham | |
| 2009/0198233 A1 | 8/2009 | Chojin | |
| 2009/0209957 A1 | 8/2009 | Schmaltz | |
| 2009/0209960 A1 | 8/2009 | Chojin | |
| 2009/0234354 A1 | 9/2009 | Johnson | |
| 2009/0248021 A1 | 10/2009 | McKenna | |
| 2010/0016857 A1 | 1/2010 | McKenna | |
| 2010/0036375 A1 | 2/2010 | Regadas | |
| 2010/0042140 A1 | 2/2010 | Cunningham | |
| 2010/0042143 A1 | 2/2010 | Cunningham | |
| 2010/0049187 A1 | 2/2010 | Carlton | |
| 2010/0057081 A1 | 3/2010 | Hanna | |

(Continued)

FOREIGN PATENT DOCUMENTS

CA    2104423    2/1994

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

Primary Examiner — Michael Peffley (57) ABSTRACT

A forceps includes a housing having a shaft attached thereto and an end effector assembly disposed at a distal end thereof. The shaft has a longitudinal axis defined therethrough. The end effector assembly includes a pair of jaw members disposed in opposing relation relative to one another. Each jaw member has an opposing sealing surface and at least one of the jaw members is moveable relative to the other about a pivot from a first position to a second position for grasping tissue therebetween. The pivot is positioned offset from the longitudinal axis defined through the shaft. When the jaw members are disposed in the second position, a plane is formed between the opposing sealing surfaces, the plane offset from the longitudinal axis.

19 Claims, 5 Drawing Sheets

U.S. PATENT DOCUMENTS

| | | |
|---|---|---|
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV |
| 2010/0069904 A1 | 3/2010 | Cunningham |
| 2010/0069953 A1 | 3/2010 | Cunningham |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0094287 A1 | 4/2010 | Cunningham |
| 2010/0100122 A1 | 4/2010 | Hinton |
| 2010/0145334 A1 | 6/2010 | Olson |
| 2010/0177071 A1 | 7/2010 | Chu |
| 2010/0179545 A1 | 7/2010 | Twomey |
| 2010/0179546 A1 | 7/2010 | Cunningham |
| 2010/0179547 A1 | 7/2010 | Cunningham |
| 2010/0249776 A1 | 9/2010 | Kerr |
| 2010/0256635 A1 | 10/2010 | McKenna |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

VESSEL SEALING JAW WITH OFFSET SEALING SURFACE

BACKGROUND

The present disclosure relates to surgical instruments. More particularly, the present disclosure relates to forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a forceps including a housing having shaft attached thereto. The shaft has a longitudinal axis defined therethrough and an end effector assembly disposed at a distal end thereof. The end effector assembly includes a pair of jaw members disposed in opposing relation relative to one another. Each jaw member has an opposing sealing surface and one or both of the jaw members is moveable relative to the other about a pivot from a first position to a second position for grasping tissue therebetween. The pivot is positioned either coincident or offset from the longitudinal axis defined through the shaft. When the jaw members are disposed in the second position, a plane is formed between the opposing sealing surfaces of each of the jaw members. The plane is configured to be positioned offset from the longitudinal axis.

In one embodiment, the pivot is offset a distance "X" relative the longitudinal axis, where "X" is preferably in the range of about 0.036" to about 0.046".

In another embodiment, the plane formed between the opposing sealing surfaces is offset a distance "Y" relative to the longitudinal axis, where "Y" is preferably in the range of about 0.005" to about 0.025".

In yet another embodiment, the forceps further includes a knife assembly disposed within the shaft and a knife channel defined within one or both of the jaw members. Upon activation, a knife blade is configured to translate distally from the shaft and extend at least partially through the knife channel(s) to cut tissue disposed between the jaw members. The knife blade may be configured such that when the knife blade is translated distally from the shaft through the knife channel(s), the knife blade is offset a distance "Z" relative to the pivot.

In still yet another embodiment, the forceps further includes at least one handle that operably couples to a drive assembly for moving the jaw members between the first and second positions. One or both of the jaw members may be adapted to connect to an electrosurgical energy source to communicate energy to tissue disposed between the jaw members.

In accordance with another embodiment of the present disclosure, a forceps is provided including a housing having a shaft attached thereto. The shaft has a longitudinal axis defined therethrough and an end effector assembly disposed at a distal end thereof. The end effector assembly includes first and second jaw members disposed in opposing relation relative to one another. Each jaw member includes a sealing surface opposed to the sealing surface of the opposing jaw member. The first jaw member is moveable relative to the second jaw member about a pivot from a first position to a second position for grasping tissue therebetween. The sealing surface of the second jaw member is offset relative to the longitudinal axis defined through the shaft.

In one embodiment, the sealing surface of the first jaw member has a thickness "T" that forms a substantially parallel plane beyond the longitudinal axis and toward the opposing sealing surface. The thickness "T" may be in the range of about 0.105" to about 0.120".

BRIEF DESCRIPTION OF THE DRAWINGS

Various embodiments of the presently disclosed forceps are described herein with reference to the drawings, wherein.

DETAILED DESCRIPTION

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 1:
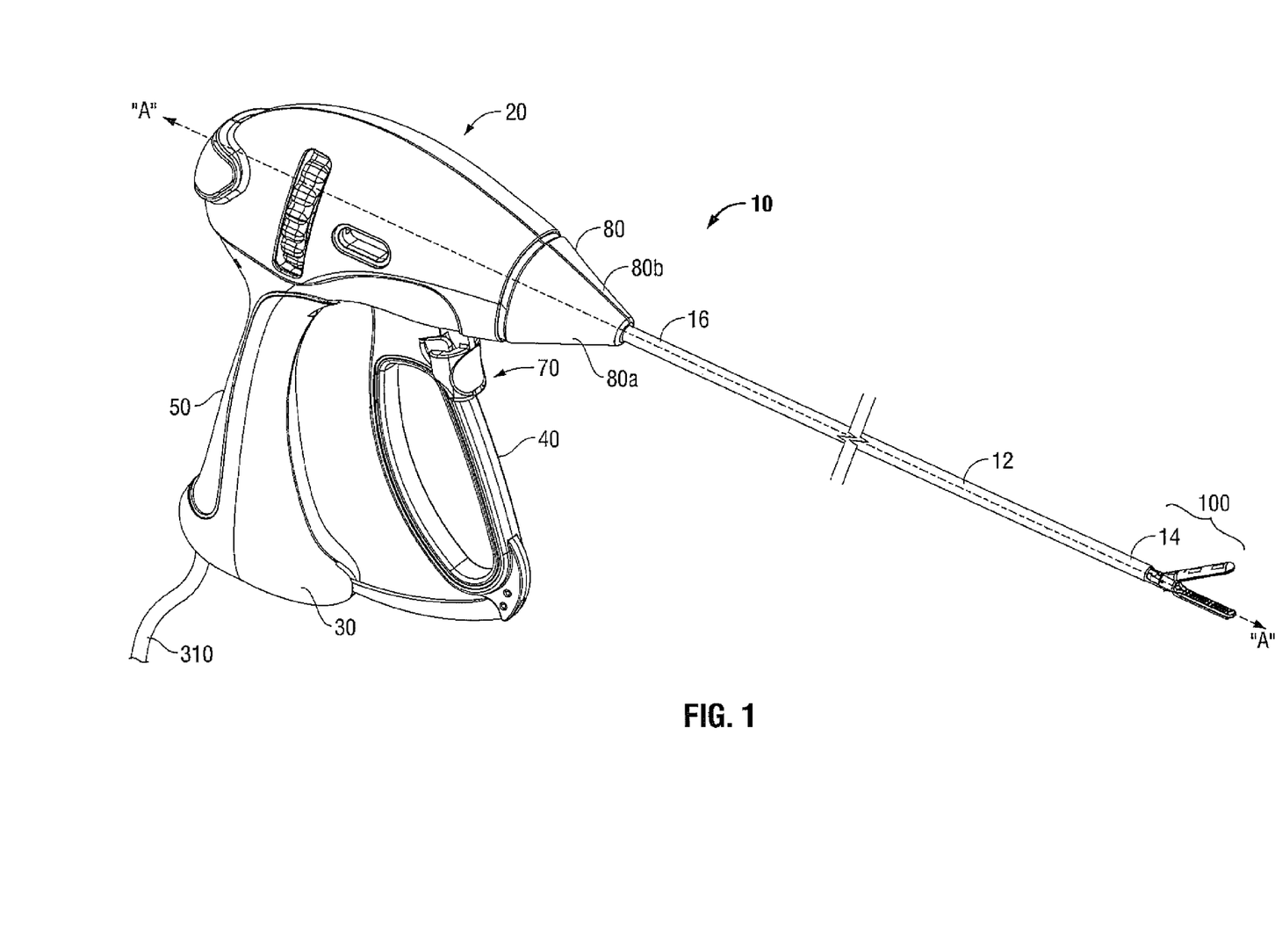
FIG. 1 is a perspective view of a surgical instrument having an end effector assembly in accordance with an embodiment of the present disclosure.

Turning now to FIG. 1, a forceps 10 is provided including a housing 20, a handle assembly 30, a rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown). Cable 310 has sufficient length to extend through shaft 12 in order to provide electrical energy to at least one of jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 80 is integrally associated with housing 20 and is rotatable approximately 180 degrees in either direction about a longitudinal axis "A." The housing 20 includes two halves that house the internal working components of the forceps 10 (see FIG. 5).

Figure 2:
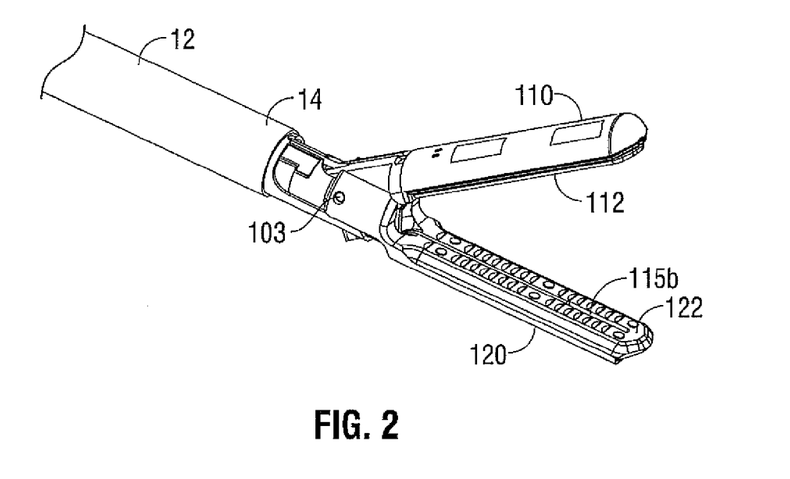
FIG. 2 is a perspective view of an end effector assembly in accordance with an embodiment of the present disclosure.

Turning now to FIG. 2, end effector assembly 100 is shown attached at a distal end 14 of shaft 12 and includes a pair of opposing jaw members 110 and 120. Each of jaw members 110 and 120 includes a sealing surface 112 and 122, respectively, that is dimensioned to oppose the other as shown in FIG. 2. End effector assembly 100 is designed as a unilateral assembly, i.e. jaw member 120 is fixed relative to the shaft 12 and jaw member 110 is moveable about a pivot 103 relative to jaw member 120. Moveable handle 40 of handle assembly 30 (see FIG. 1) is ultimately connected to a drive assembly 150 (see FIG. 5) that, together, mechanically cooperate to impart movement of jaw members 110 and 120 from an open position to a clamped position to grasp tissue between sealing surfaces 112 and 122.

As illustrated in FIG. 2, a knife channel half 115b is defined through the center of jaw member 120. A corresponding knife channel half (not shown) is defined through the center of jaw member 110. When jaw members 110 and 120 are disposed in the clamped position, the knife channel halves together form a complete knife channel 115 (see FIG. 3B), such that a blade 185 of a knife assembly 140 (see FIG. 4) can translate distally therethrough cutting tissue grasped between the jaw members 110 and 120.

Figure 3A:
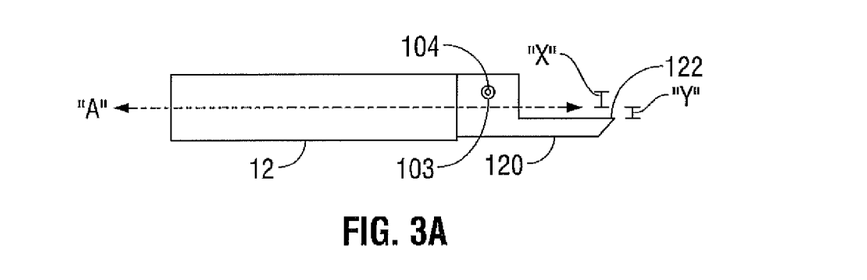
FIG. 3A is a schematic view of an end effector assembly in accordance with one embodiment of the present disclosure in which the upper jaw member has been removed.
Figure 3B:
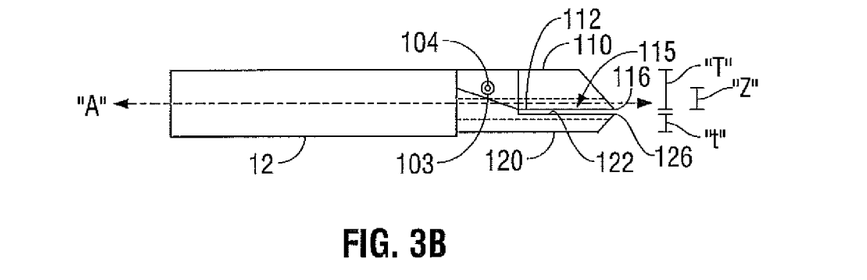
FIG. 3B is a schematic view of the end effector assembly of FIG. 3A where the upper jaw member has been replaced.

With reference now to FIGS. 3A-B, end effector assembly 100 is shown in accordance with one embodiment of the present disclosure. End effector assembly 100 is mechanically engaged to shaft 12, that defines a longitudinal axis "A" therethrough. Jaw member 120 is fixed relative to shaft 12 and jaw member 110 is moveable relative to jaw member 120 about pivot 103. As shown, pivot 103 is offset above longitudinal axis "A" creating a greater mechanical advantage on jaw member 110 as compared to a configuration where the pivot is positioned on the longitudinal axis. The positioning of pivot 103 offset above longitudinal axis "A" as shown in FIGS. 3A-3B, also allows knife blade 185 to pass under pivot pin 104 when the knife blade 185 is advanced distally to cut tissue between jaw member 110 and 120. More specifically, pivot 103 may be positioned such that knife blade 185 passes a distance "Z" below the pivot pin 104. Additionally, pivot 103 may be positioned a distance "X" above the longitudinal axis "A" where "X" is in the range of about 0.036" to about 0.046" to optimize the mechanical advantage and provide an enhanced and uniform tissue seal. However, it is also contemplated that different surgical procedures and/or different surgical instruments may require the pivot 103 to be positioned a distance "X" above the longitudinal axis "A," where "X" is outside of the range stated above.

With continued reference to FIGS. 3A-3B, fixed jaw member 120 may be configured such that sealing surface 122 of jaw member 120 lies below longitudinal axis "A." Sealing surface 122 may be positioned a distance "Y" below the longitudinal axis "A" where "V" is preferably in the range of about 0.005" to about 0.025". However, it is also contemplated that sealing surface 122 be positioned below the longitudinal axis "A" a distance outside the range stated above, depending on the surgical instrument to be used and/or the surgical procedure to be performed. As a result of sealing surface 122 being positioned below the longitudinal axis "A," when moveable jaw member 110 is moved into the clamped position to grasp tissue therebetween, the plane created between sealing surfaces 112 and 122 lies below longitudinal axis "A." In order to achieve this result, fixed jaw member 120 may be manufactured with less material, having a thickness "t," as compared to moveable jaw member 110, that may be manufactured with more material and have a thickness "T," greater than the thickness "t" of jaw member 120. In other words, no additional material would be required to manufacture jaw members 110 and 120 in the above-configuration than would be required if jaw members 110 and 120 had equal thickness. Rather, in theory, the material that is taken from fixed jaw 120 is supplemented to movable jaw 110. Fixed jaw 120 remains strong due to the solid core construction thereof, while the strength of moveable jaw 110 is bolstered by the additional material. Such a configuration is advantageous given the forces applied to moveable jaw 110 as a result of the repeated movement of jaw member 110 between the open and the clamped position.

The thickness "t" of fixed jaw member 120 may be in the range of about 0.075" to about 0.095", while the thickness "T" of moveable jaw member 120 may be in the range of about 0.105" to about 0.120", although other thicknesses "t" and "T" are contemplated depending on the instrument to be used and/or the procedure to be performed.

The combination of the offset pivot 103 about the longitudinal axis "A" and the bottom seal plate 122 being disposed below the longitudinal axis "A" produces a tip-biased jaw design which enhances a uniform and consistent seal. In other words, during the movement to the closed and grasping configuration, the distal tips 116 and 126 of jaw members 110 and 120, respectively, come into contact with one another first and the closure pressure transferred to the jaw members 110 and 120 by drive assembly 150 deflects the proximal portion of jaw member 110 into contact with jaw member 120 thereafter. Manufacturing the jaw members 110 and 120 in this fashion creates a more uniform pressure distribution along the jaw members 110 and 120 which enhances a tissue seal.

Figure 4:
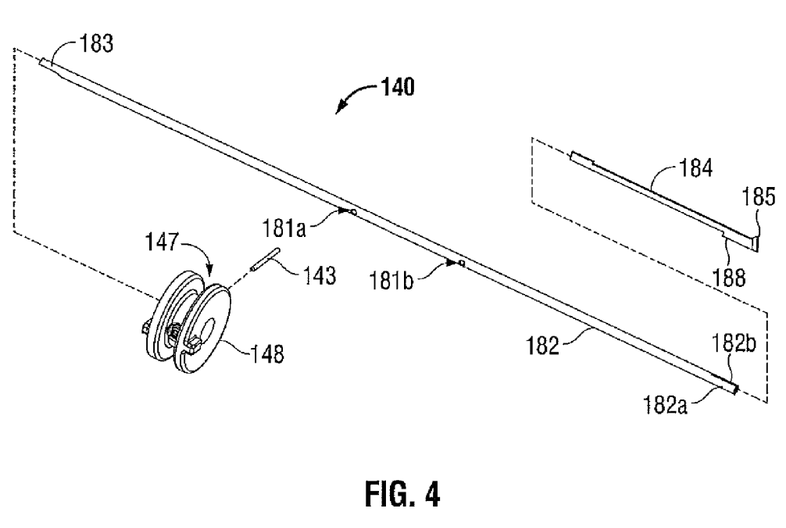
FIG. 4 is an exploded, perspective view of the knife assembly in accordance with one embodiment of the present disclosure.
Figure 6:
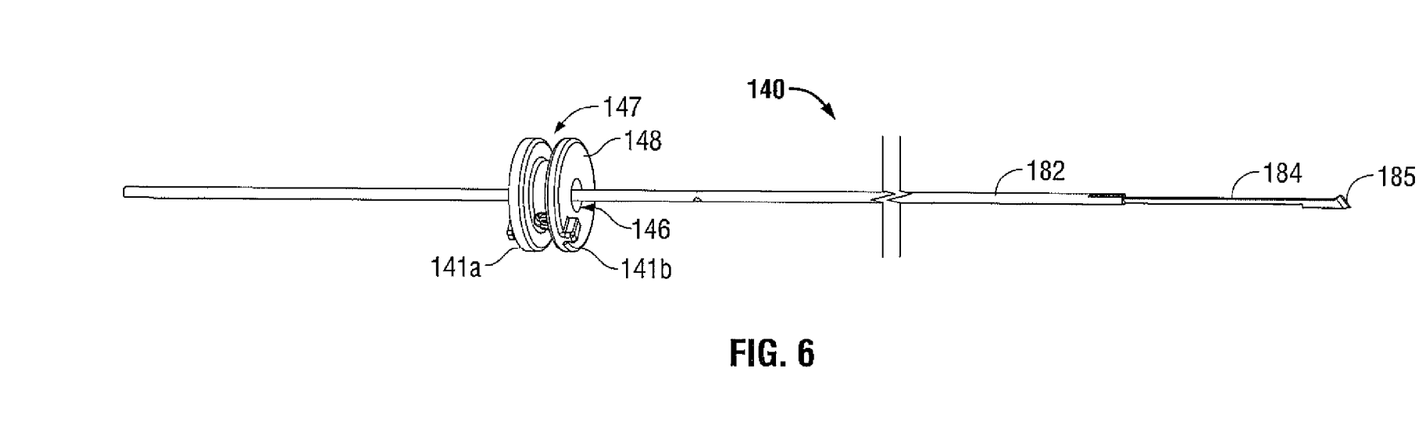
FIG. 6 is a perspective view of the knife assembly of FIG. 4.

Referring now to FIGS. 4 and 6, knife assembly 140 is shown including knife rod 182, knife bar 184 and knife wheel 148. Knife rod 182 has a bifurcated distal end comprising prongs 182a and 182b that cooperate to receive knife bar 184 therein. The knife assembly 140 also includes a proximal end 183 that is keyed to facilitate insertion into tube 160 of rotating assembly 80 (see FIG. 7). Knife wheel 148 is secured to the knife bar via pin 143. Knife wheel 148 includes rings 141a and 141b that define a drive slot 147 therebetween. The knife rod 182 includes apertures 181a and 181b; aperture 181a is used, as shown, to receive and secure the knife wheel 148 to the knife rod 182 via pin 143 such that longitudinal reciprocation of the knife wheel 148, in turn, moves the knife rod 182. Knife bar 184 includes knife support 188 at a distal end thereof, with knife blade 185 being welded to knife support 188.

Figure 5:
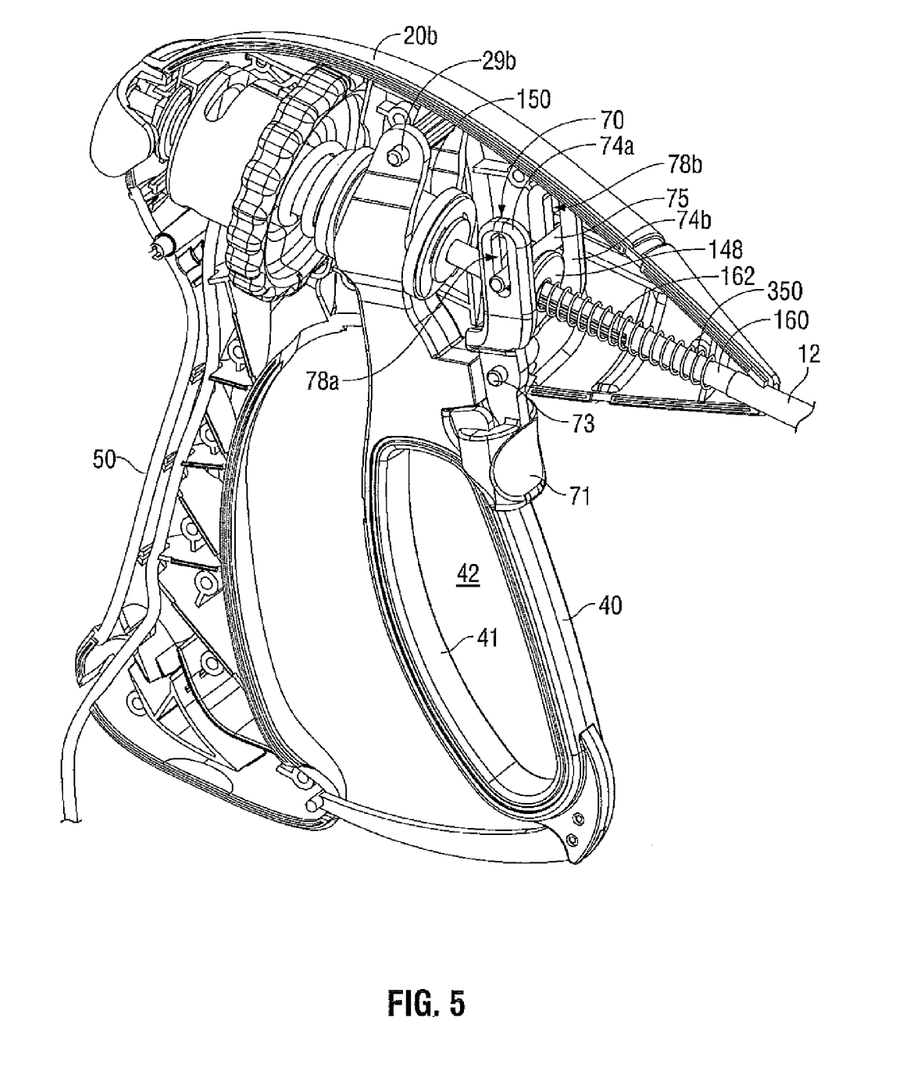
FIG. 5 is a perspective view of the housing with half of the housing enclosure removed.

Referring now to FIG. 5, which shows the details of the housing 20 and the internal components thereof, namely, the drive assembly 150, the trigger assembly 70, and the handles 40 and 50. More particularly, FIG. 5 shows the above-identified assemblies and components in an assembled form in the housing 20.

As shown in FIG. 5, trigger assembly 70 cooperates with the knife assembly 140 (see FIG. 4) to selectively translate knife 185 through knife channel 115 (see FIG. 3). The trigger assembly 70 includes a finger actuator 71 and a U-shaped upwardly-extending flange 74 having legs 74a and 74b. A pivot pin 73 mounts the trigger assembly 70 between housing halves 20a and 20b for selective rotation thereof. Legs 74a and 74b of the U-shaped flange 74 each include a respective slot 78a and 78b defined therein that are each dimensioned to receive a free end of an elongated drive bar 75. Drive bar 75, in turn, is dimensioned to sit within a drive slot 147 (see FIG. 4) defined in knife assembly 140 explained above. The trigger assembly 70 is mounted atop the knife wheel 148 of the knife assembly 140. Proximal activation of the finger actuator 71 rotates the trigger assembly 70 about pivot pin 73 which, in turn, forces the drive bar 75 distally to ultimately extend the knife 185 through knife channel 115. A spring 350 biases the knife assembly 140 in a retracted position such that once advancement of the knife 185 is complete, the knife 185 and the knife assembly 140 are automatically returned to a proximal pre-firing position.

Figure 7:
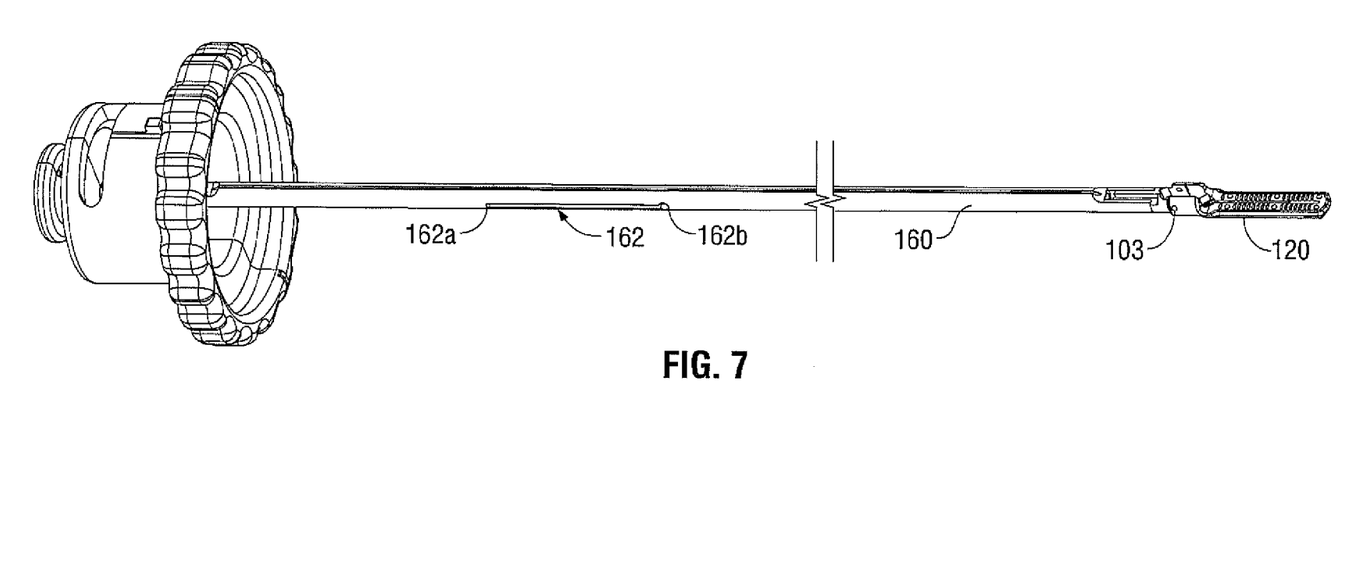
FIG. 7 is a perspective view of the lower jaw member and rotating assembly in accordance with the present disclosure.

Turning now to FIGS. 6-7, knife assembly 140, as discussed in detail above, is shown including knife wheel 148 engaging aperture 181a of knife rod 182. Upon assembly of forceps 10, knife rod 182 is inserted into tube 160, whereby knife wheel 148 surrounds tube 160 with pin 143 passing through slot 162 of tube 160 and aperture 181a of knife rod 182, mechanically engaging knife wheel 148 thereon. As discussed above, proximal activation of finger actuator 71 causes longitudinal reciprocation of knife wheel 148, which, in turn, moves knife rod 182 distally as pin 143 translates distally along slot 162 of tube 160.

Slot 162 of tube 160 includes proximal end 162a and distal end 162b. Slot 162 may be dimensioned so that proximal end 162a acts as a stop for pin 143 as knife rod 182 is retracted proximally, providing the at-rest position of knife rod 182. In such a configuration, after actuation of knife 185, knife wheel 148 and therefore knife 185 are retracted proximally until pin 143 contacts proximal end 162a of slot 160, thereby preventing further movement thereof. Accordingly, pin 143 absorbs the retract force as knife wheel 148 retracts under force from spring 350 and slot end 162a prevents further proximal retraction. Pin 143 would thus remain in an at-rest position, at proximal end 162a of slot 162 under the biasing force from spring 350 until finger actuator 71 is activated, thereby advancing knife 185 distally, as described above. As such, the proximal end 162a of shaft 162 may be configured to prevent proximal translation of the knife 185 beyond a proximal end of the knife channel 115 thereby preventing a potential misfire of the knife blade 185.

More particularly, the proximal end 162a of slot 162 prevents the knife blade 185 from retracting proximally beyond the proximal end of the knife channel 115 assuring that, upon activation, the knife blade 185 will advance properly within the knife channel 115 and through tissue. Maintaining the knife blade 185 within the proximal end of the knife channel 115 also prevents unnecessary damage to the knife blade 185 and essentially eliminates mis-firing.

Although the foregoing disclosure has been described in some detail by way of illustration and example, for purposes of clarity or understanding, it will be obvious that certain changes and modifications may be practiced within the scope of the appended claims.

What is claimed:

1. A forceps, comprising:
    a shaft having a longitudinal axis defined therethrough and an end effector assembly disposed at a distal end thereof, the end effector assembly including:
        a pair of jaw members disposed in opposing relation relative to one another, each jaw member having an opposing sealing surface, at least one jaw member pivotable relative to the other about a pivot pin from a first position to a second position for grasping tissue therebetween;
        wherein the pivot pin is offset in a first direction from the longitudinal axis; and
        wherein, when the jaw members are disposed in the second position, a plane is formed between the opposing sealing surfaces, the plane offset in a second, opposite direction from the longitudinal axis.

2. The forceps according to claim 1, wherein the pivot pin is offset a distance "X" relative to the longitudinal axis, wherein "X" is in the range of about 0.036" to about 0.046".

3. The forceps according to claim 1, wherein the plane is offset a distance "Y" relative to the longitudinal axis, wherein "Y" is in the range of about 0.005" to about 0.025".

4. The forceps according to claim 1, further comprising a knife assembly disposed within the shaft and a knife channel defined within at least one of the jaw members wherein, upon activation, a knife blade is configured to translate distally from the shaft and extend at least partially through the at least one knife channel to cut tissue disposed between the jaw members.

5. The forces according to claim 4, wherein when the knife blade is translated distally from the shaft and at least partially through the at least one knife channel, the knife blade is offset a distance "Z" relative to the pivot pin.

6. The forceps according to claim 1, wherein the forceps includes at least one handle that operably couples to a drive assembly for moving the jaw members between the first and second positions.

7. The forceps according to claim 1, wherein at least one of the jaw members is adapted to connect to an electrosurgical energy source to communicate energy to tissue disposed between the jaw members.

8. The forceps according to claim 1, wherein one of the jaw members is fixed relative to the shaft and the other jaw member is pivotable about the pivot pin and relative to the fixed jaw member and the shaft between the first and second positions.

9. The forceps according to claim 8, wherein the pivot pin is offset relative to the longitudinal axis in a direction towards the pivotable jaw member and wherein the plane is offset relative to the longitudinal axis in a direction towards the fixed jaw member.

10. A forceps, comprising:
    a shaft having a longitudinal axis defined therethrough and an end effector assembly disposed at a distal end thereof, the end effector assembly including:
        first and second jaw members disposed in opposing relation relative to one another, each jaw member including a sealing surface opposed to the sealing surface of the opposing jaw member, the second jaw member fixed relative to the shaft, the first jaw member pivotable relative to the second jaw member about a pivot pin from a first position to a second position for grasping tissue therebetween;

wherein the pivot pin is offset in a first direction relative to the longitudinal axis and wherein the sealing surface of the second jaw member defines a first plane that is offset in a second, opposite direction relative to the longitudinal axis.

11. The forceps according to claim 10, wherein the first, pivotable jaw member includes a thickness "T" such that the sealing surface of the first, pivotable jaw member forms a substantially parallel second plane beyond the longitudinal axis and toward the opposing sealing surface.

12. The forceps according to claim 11, wherein the thickness "T" is in the range of about 0.105" to about 0.120".

13. The forceps according to claim 11, wherein the second, fixed jaw member defines a thickness "t" that is smaller than the thickness "T" of the first, pivotable jaw member.

14. The forceps according to claim 13, wherein the thickness "t" is in the range of about 0.0075" to about 0.095".

15. The forceps according to claim 10, wherein the pivot pin is offset relative to the longitudinal axis in a direction towards the pivotable jaw member and wherein the sealing surface of the second jaw member is offset relative to the longitudinal axis in a direction towards the second jaw member.

16. A forceps, comprising:
a shaft defining a longitudinal axis;
an end effector assembly disposed at a distal end of the shaft, the end effector assembly including:
first and second jaw members pivotably coupled to one another about a pivot pin, each jaw member defining an opposed sealing surface, at least one of the jaw members pivotable relative to the other between an open position and a clamped position for grasping tissue therebetween, wherein, in the clamped position, a plane is formed between the opposed sealing surfaces, and
wherein, the longitudinal axis extends between the pivot pin and the plane.

17. The forceps according to claim 16, wherein the first jaw member defines a thickness "T" and wherein the second jaw member defines a thickness "t" that is smaller than the thickness "T."

18. The forceps according to claim 17, wherein the plane is offset a distance "Y" relative to the longitudinal axis, and wherein the distance "Y" is equal to a difference between the thickness "T" the thickness "t."

19. The forceps according to claim 16, wherein the second jaw member is fixed relative to the shaft and wherein the first jaw member is pivotable relative to the second jaw member and the shaft.

* * * * *